United States Patent
Shastri et al.

(10) Patent No.: US 11,450,323 B1
(45) Date of Patent: Sep. 20, 2022

(54) SEMANTIC REPORTING SYSTEM

(71) Applicants: Kaushal Shastri, Stamford, CT (US);
Gerard Muro, Southport, CT (US)

(72) Inventors: Kaushal Shastri, Stamford, CT (US);
Gerard Muro, Southport, CT (US)

( * ) Notice: Subject to any disclaimer, the term of this patent is extended or adjusted under 35 U.S.C. 154(b) by 289 days.

(21) Appl. No.: 16/835,594

(22) Filed: Mar. 31, 2020

Related U.S. Application Data

(60) Provisional application No. 62/827,288, filed on Apr. 1, 2019.

(51) Int. Cl.
| | | |
|---|---|---|
| G10L 15/00 | (2013.01) | |
| G10L 15/26 | (2006.01) | |
| G10L 15/18 | (2013.01) | |
| G06Q 20/14 | (2012.01) | |
| G06N 3/08 | (2006.01) | |

(52) U.S. Cl.
CPC .............. *G10L 15/26* (2013.01); *G06Q 20/14* (2013.01); *G10L 15/1815* (2013.01); *G06N 3/08* (2013.01)

(58) Field of Classification Search
CPC ..... G10L 15/19; G10L 15/26; G10L 15/1815; G06N 3/08; G06Q 20/14
USPC ........................................................ 704/235
See application file for complete search history.

(56) References Cited

U.S. PATENT DOCUMENTS

| | | | | |
|---|---|---|---|---|
| 7,302,383 B2 * | 11/2007 | Valles | ..................... | G06F 40/30 704/231 |
| 7,383,172 B1 * | 6/2008 | Jamieson | ................ | G06F 40/30 704/9 |
| 7,389,234 B2 * | 6/2008 | Schmid | ................... | G10L 15/28 704/270.1 |
| 7,996,225 B2 * | 8/2011 | Schmid | ................. | G10L 15/193 704/260 |
| 8,682,661 B1 * | 3/2014 | Schalkwyk | ......... | G10L 15/1815 704/235 |
| 8,712,772 B2 * | 4/2014 | Oez | ....................... | G06F 40/174 715/224 |
| 9,431,003 B1 * | 8/2016 | Cecchi | .................... | G10L 13/08 |
| 11,257,592 B2 * | 2/2022 | Perera | .................... | G16H 50/20 |
| 2001/0003183 A1 * | 6/2001 | Thompson | .......... | G06F 16/2428 |
| 2002/0143529 A1 * | 10/2002 | Schmid | ................. | G10L 15/193 704/E15.022 |

(Continued)

*Primary Examiner* — Khai N. Nguyen
(74) *Attorney, Agent, or Firm* — Morgan, Lewis & Bockius, LLP

(57) ABSTRACT

Speech is digitized and analyzed by a speech-recognition platform to produce raw text sentences. In various embodiments, the recognized words of each sentence are tokenized based on a grammar, which may be selected by a Recognition Context Controller (RCC) using a context database. A Medical Context Semantic Library (MCSL) contains all medically relevant terms recognized by the system and, once the grammar is selected, the MCSL is used to select a semantic template (consisting of one or more hierarchically organized data structures whose root is a "Concept"). Recognized words are mapped to tokens based on the operative grammar to fill the Concept tree(s). The grammar and the Concept trees can potentially shift after each sentence based on the RCC's analysis. The trees accumulate and are filled as sentences are analyzed. Once all of the sentences have been analyzed, the trees have been filled to the extent possible. Concepts may be organized into higher-level Observations. These observations are used to generate final reports.

18 Claims, 2 Drawing Sheets

(56) References Cited

U.S. PATENT DOCUMENTS

| | | | |
|---|---|---|---|
| 2004/0083092 A1* | 4/2004 | Valles | G06F 40/30 |
| | | | 704/9 |
| 2008/0243483 A1* | 10/2008 | Schmid | G10L 15/28 |
| | | | 704/E15.001 |
| 2012/0022865 A1* | 1/2012 | Milstein | H04M 3/42221 |
| | | | 704/235 |
| 2012/0166180 A1* | 6/2012 | Au | G06F 40/237 |
| | | | 704/9 |
| 2013/0262113 A1* | 10/2013 | Oz | G06F 40/174 |
| | | | 704/235 |
| 2016/0343367 A1* | 11/2016 | Cecchi | G10L 13/08 |
| 2018/0068076 A1* | 3/2018 | Farri | G16H 10/20 |
| 2019/0065464 A1* | 2/2019 | Finley | G06F 40/169 |
| 2020/0273573 A1* | 8/2020 | Perera | G06N 3/0454 |

* cited by examiner

SEMANTIC REPORTING SYSTEM

CROSS-REFERENCE TO RELATED APPLICATION

This application claims priority to, and the benefits of, U.S. Provisional Application No. 62/827,288, filed on Apr. 1, 2019, the entire disclosure of which is incorporated by reference herein.

FIELD OF THE INVENTION

The present invention relates generally to speech recognition, and in particular to medical dictation systems that utilize context information for transcription accuracy.

BACKGROUND

Continuous speech recognition is useful for converting spoken words into written text. Speech-recognition systems, such as dictation systems, receive an acoustic signal from a microphone, analyze the signal, and convert it into text. In healthcare applications, voice-dictation systems convert physicians' speech into reports, typically in plain-text (or free-text) format without semantic analysis or attempts to disambiguate homonyms or "sound alike" words. As a result, the transcription is useful primarily for other clinicians, who will be able to contextualize errors and inconsistencies, but not for non-specialists or automated analysis systems.

Even though structured reports with consistent templates have been introduced, portions of such reports are still typically represented in plain text. Sources of possible error are numerous. One type of error arises from different ways of expressing the same concept. For example, physicians may say the same thing in different ways or using different vocabularies (e.g., "facial nerve is normal" vs. "7th cranial nerve is normal"; "there are white matter T1 hyperintensities" vs. "there are t1 white matter hyperintensities" vs. "there are hyperintensities on the t1 weighted sequence in the brain white matter"). Physicians often employ different dictation styles and different organizational preferences for the body of a report. Subtle voice-recognition errors, even if checked by the physician, may propagate through to the report (e.g., "atypical T2 signal" vs "a typical t2 signal"). Specialists may also employ "hedging language," which is confusing; for example, this may arise when a radiologist is unable to discern the underlying abnormality from the images. Another well-known and much-lamented source of error in medical reports is improper selection of billing codes by non-clinical personnel.

Accordingly, there is a need for more sophisticated medical-dictation systems capable of, for example, creating reports with consistent meanings despite differences in dictation style or vocabulary; creating complete reports without missing items; and creating clear reports with readily identified information.

SUMMARY

Embodiments of the invention control the dictation vocabulary, convert various ways of saying the same thing into a single representation, and convert all words into a computational representation that reflects semantic meaning, enabling the computer to create consistency, completeness, and clarity of the content dictated by the physician. It is unnecessary to utilize complex machine-learning algorithms or approaches, such as neural networks.

In broad overview, speech is digitized and analyzed by a speech-recognition platform to produce raw text sentences. The recognized words of each sentence are tokenized based on a grammar, which, in various embodiments, is selected by a Recognition Context Controller (RCC) using a context database. A Medical Context Semantic Library (MCSL) contains all medically relevant terms recognized by the system and, once the grammar is selected, the MCSL is used to select a semantic template (consisting of one or more hierarchically organized data structures whose root is a "Concept"). Recognized words are mapped to tokens based on the operative grammar to fill the Concept tree(s). The grammar and the Concept trees can potentially shift after each sentence based on the RCC's analysis. The trees accumulate and are filled as sentences are analyzed. Once all of the sentences have been analyzed, the trees have been filled to the extent possible. Concepts may be organized into higher-level Observations on a sentence-by-sentence basis. These observations may be used to generate final reports.

Accordingly, in a first aspect, the invention relates to a medical dictation system. In various embodiments, the system comprises a processor; circuitry for converting digitized speech into a digitized representation; a memory for storing the digitized speech as raw text; a semantic context database for storing a plurality of grammars; a speech platform for parsing the digitized speech into tokens based on one of the stored grammars; a recognition context control module, executable by the processor, for analyzing the tokens and retaining, altering or replacing the grammar based on the tokens; a medical concept semantic library configured for electronic storage of a plurality of semantic templates, where each of the semantic templates comprises a plurality of hierarchical data structures each including a root node corresponding to a top-level medical concept and at least one subsidiary node, and the speech platform is further configured to fill the nodes of the data structures with at least some of the tokens; and a facility for transforming the data structures into a structured narrative report.

In various embodiments, the recognition context controller is configured to retain, alter or replace the grammar based on raw text corresponding to words of one or more dictated sentences by searching the semantic context database for entries matching the words. The processor may be configured to analyze the raw text during an interval between spoken sentences. The facility may comprise a semantic observation generation system, executable by the processor and configured to generate observation data structures by classifying each of the data structures as a main concept or an associated concept, and organizing the classified data structures into hierarchical Observationitem data structures, each of the Observationitem data structures including a KeyConcept root node corresponding to the main concept and child nodes corresponding to the associated concepts.

In some embodiments, the main concept corresponds to one of (i) an abnormal or normal finding, (ii) anatomical area, (iii) diagnosis, (iv) devices and device components, (v) change from a previous report, and (vi) follow-up recommendation. The recognition context control module may be responsive to tokens in the Observationitem data structures in determining whether to alter or replace a current grammar. Follow-up recommendations may be pre-loaded in main concept data structures.

The system may also include a facility for receiving text corresponding to at least one of a reason for examination, a patient history, or information corresponding to an imaging modality and converting the text into tokens for assignment to the nodes of the data structures. The system may further include a clinical scoring module, executable by the processor, for generating clinical scores based on the observation data structures and/or a code-generation module, executable by the processor, for generating billing codes based on the observation data structures.

In another aspect, the invention relates to a method of computationally transcribing medical dictation. In various embodiments, the method comprises the steps of converting dictated speech into a digitized representation; electronically storing the digitized speech as raw text; electronically storing, in a semantic context database, a plurality of grammars; electronically storing a plurality of semantic templates, each of the semantic templates comprising a plurality of hierarchical data structures each including a root node corresponding to a top-level medical concept and at least one subsidiary node; computationally parsing the digitized speech into tokens based on one of the stored grammars; computationally analyzing the tokens and retaining, altering or replacing the grammar based on the tokens; filling the nodes of the data structures with at least some of the tokens; and transforming the data structures into a structured narrative report.

In some embodiments, the method further includes retaining, altering or replacing the grammar based on raw text corresponding to words of one or more dictated sentences by searching the semantic context database for entries matching the words. The step of computationally parsing may occur during an interval between spoken sentences.

In various embodiments, observation data structures are generated according to steps comprising classifying each of the data structures as a main concept or an associated concept; and organizing the classified data structures into hierarchical Observationitem data structures, each of the Observationitem data structures including a KeyConcept root node corresponding to the main concept and child nodes corresponding to the associated concepts. The main concept may correspond to one of (i) an abnormal or normal finding, (ii) anatomical area, (iii) diagnosis, (iv) devices and device components, (v) change from a previous report, and (vi) follow-up recommendation. Determining whether to alter or replace a current grammar may be based at least in part on tokens in the Observationitem data structures. Follow-up recommendations may be pre-loaded in main concept data structures.

In some embodiments, the method further comprises the steps of receiving text corresponding to at least one of a reason for examination, a patient history, or information corresponding to an imaging modality and computationally converting the text into tokens for assignment to the nodes of the data structures. The method may include computationally generating clinical scores based on the observation data structures and/or computationally generating billing codes based on the observation data structures.

In general, as used herein, the term "substantially" means±10%, and in some embodiments, ±5%. In addition, reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
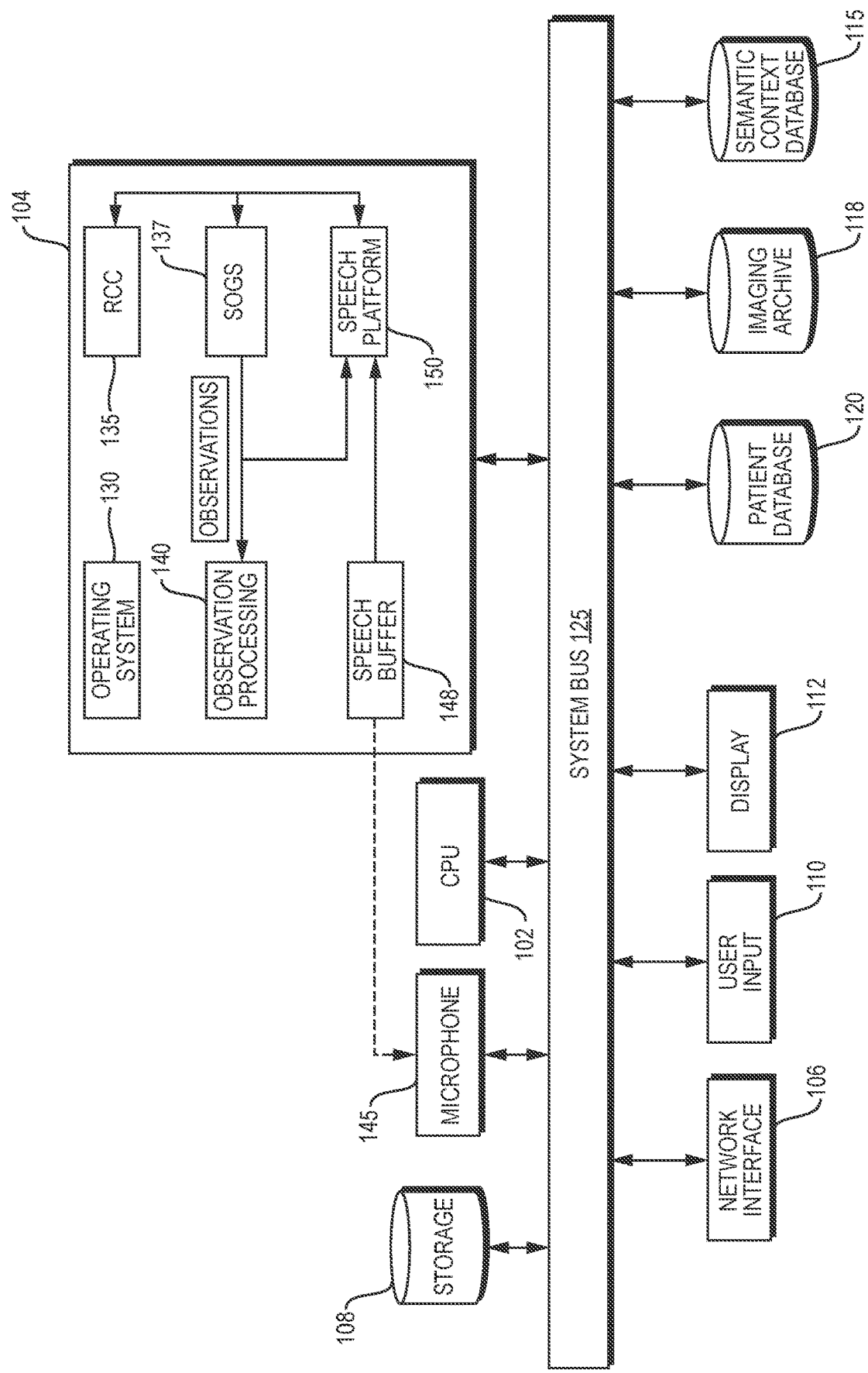
FIG. 1 schematically illustrates a representative hardware architecture implementing embodiments of the invention.

Refer first to FIG. 1, which illustrates a representative hardware implementation of a system embodying the invention. The system 100 includes a processor 102 (e.g., a CPU microprocessor) and associated system memory 104, a network interface 106, and, usually, one or more non-volatile digital storage elements 108 (such as a hard disk, CD, DVD, USB memory key, etc.) and associated drives. Further, system 100 includes one or more conventional user input devices such as a keyboard and a mouse or touch pad, as well as a display screen 112. A wireless interface, which may be separate from or implemented within network interface 106, facilitates wireless communication with, e.g., user mobile devices or wireless audio sensors. The system also includes a pair of databases 115, 118, which are described in detail below. Briefly, semantic context database 115 contains terminology sets corresponding to different grammars, which the system uses as context to parse spoken sentences that have been converted into raw text; imaging archive 118 contains information regarding acquired medical images relevant to the patients whose medical information is stored in database 120, i.e., who have been registered with system 100. Databases 115, 118, 120 may be local to system 100 or may be remote, with data retrieved and stored via network interface 106. The various components communicate with each other via one or more bidirectional system buses 125.

In use, processor 102 executes one or more computer programs (conceptually illustrated as program modules) stored in system memory 104. An operating system 130 (such as, e.g., MICROSOFT WINDOWS, UNIX, LINUX, iOS, or ANDROID) provides low-level system functions, such as file management, resource allocation, and routing of messages from and to hardware devices (such as I/O devices 110, 112) and higher-level applications including a Recognition Context Controller (RCC) 135, a Semantic Observation Generation System (SOGS) 137, and an Observation Processing module 140. As the user speaks into a microphone 145, an analog-to-digital converter or operating system 130 digitizes the resulting voice signals and accumulates them in a speech buffer 148, which may be a partition of memory 104 or a separate memory device. A conventional speech platform 150, such as the MICROSOFT Speech Platform, converts the recorded speech into raw text based on a pre-loaded grammar.

The term "network" is herein used broadly to connote wired or wireless networks of computers or telecommunications devices (such as wired or wireless telephones, tablets, etc.). For example, a computer network may be a local area network (LAN) or a wide area network (WAN). When used in a LAN networking environment, computers may be connected to the LAN through a network interface or adapter; for example, a supervisor may establish communication with control system 112 using a tablet that wirelessly joins the network. When used in a WAN networking environment, computers typically include a modem or other communication mechanism. Modems may be internal or external, and may be connected to the system bus via the user-input interface, or other appropriate mechanism. Networked computers may be connected over the Internet, an Intranet, Extranet, Ethernet, or any other system that provides communications. Some suitable communications protocols include TCP/IP, UDP, or OSI, for example. For wireless communications, communications protocols may include IEEE 802.11x ("Wi-Fi"), Bluetooth, ZigBee, IrDa, near-field communication (NFC), or other suitable protocol. Furthermore, components of the system may communicate through a combination of wired or wireless paths, and communication may involve both computer and telecommunications networks.

CPU 102 is typically a microprocessor, but in various embodiments may be a microcontroller, peripheral integrated circuit element, a CSIC (customer-specific integrated circuit), an ASIC (application-specific integrated circuit), a logic circuit, a digital signal processor, a programmable logic device such as an FPGA (field-programmable gate array), PLD (programmable logic device), PLA (programmable logic array), RFID processor, graphics processing unit (GPU), smart chip, or any other device or arrangement of devices that is capable of implementing the steps of the processes of the invention.

Figure 2:
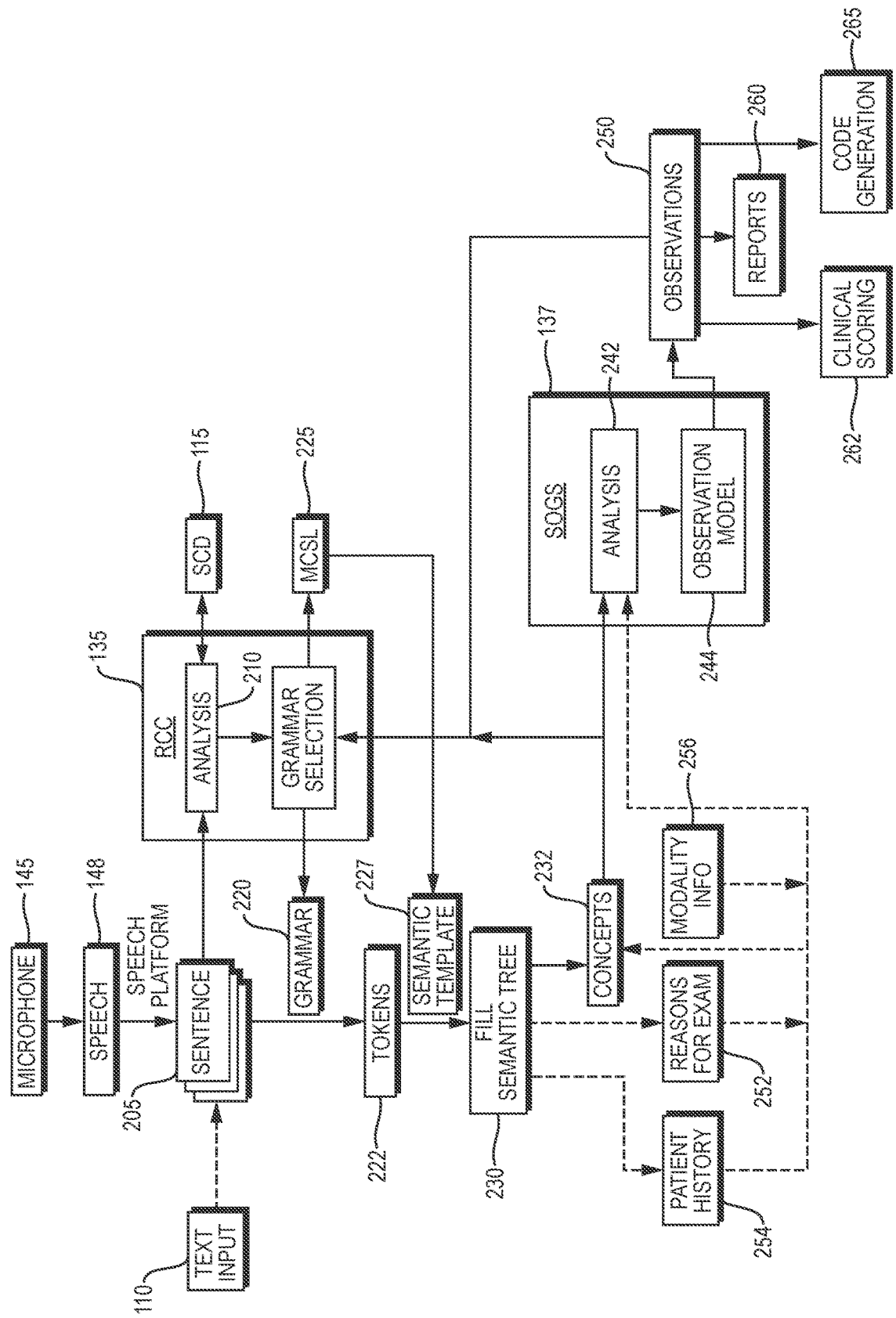
FIG. 2 schematically illustrates the workflow and key modules of an embodiment of the invention.

With reference to FIGS. 1 and 2, the stored raw text 148 generated by speech platform 150 takes the form of sentences 205, which are defined as two or more spoken words. Punctuation need not be spoken by the user, which represents an advantage of the present approach. In conventional speech-recognition systems, physicians dictate punctuation such as commas, periods, new paragraphs, semicolons, etc. because they have to be aware of the format of the text that is being generated. Physicians using systems as described herein, by contrast, may omit punctuation. Text may also be loaded as input via an input device 110. In either case, the words of a sentence are parsed, i.e., assigned to tokens having semantic content, based on a grammar that is selected based on the vocabulary employed by the user as s/he speaks.

In particular, RCC 135 includes an analysis module 210 that continuously monitors the words of the last few dictated sentences 205 and, based thereon, selects a grammar 220 (also referred to herein as the dictation context) from semantic context database (SCD) 115. That is, each time a new sentence is dictated and received by the system, analysis module 210 analyzes it along with the preceding one, two or three sentences to determine whether a context change—i.e., an exchange of one grammar for another or, in some cases, supplementing the current grammar(s) with another—is appropriate. In particular, during the physician's brief pause at the end of each sentence, analysis module 210 searches SCD 115 for entries matching words in the last few sentences of dictated raw text. If, for example, a spoken word corresponds to a higher-level construct in a different grammar, analysis module 210 may infer a context switch and either supplement or replace the current grammar with the one containing the higher-level construct. For example, the physician may have dictated an abnormality such as a cyst but not provided details in the sentence. If the current grammar includes the term "cyst" as a recognized entry with no detail categories or does not include the term at all, analysis module 210 will search for a grammar in SCD 115 in which Cyst is a high-level data construct including subsidiary categories corresponding to medical details (i.e., entries such as density, septa, solid components, etc.). Upon locating such a grammar, analysis module 210 will change effect a context change, replacing or supplementing the current grammar 220 with that of the Cyst, and then may automatically switch back to the earlier context once all the Cyst information has been dictated.

The currently active grammar is used to select templates from a medical concept semantic library (MCSL) 225, which contains all medical concepts to be recognized and processed by the system. Both grammars and the MC SL 225 may be assembled straightforwardly and without undue experimentation based on well-characterized medical vocabularies, e.g., based on RadLex (a controlled terminology for radiology described at https://healthdata.gov/datase/radlex) or LOINC (a common terminology for laboratory and clinical observations described at https://loinc.org/). In some implementations, MCSL 225 is split into multiple smaller libraries based on clinical practice or computational convenience. MCSL 225 may be implemented as a compiled set of software classes or as a database, depending on design preferences. Once the grammar 220 is selected, MCSL 225 is used to select a semantic template (consisting of one or more hierarchically organized (e.g., tree) data structures) whose root is a "Concept," i.e., a high-level medical term (e.g., an anatomic component or region, or a disease condition) whose description generally includes specific details; these details define the subsidiary (child) nodes of the tree, and the grammar, parsing the input text, reacts to their presence by loading them into the appropriate Concept data structure. The Concept data structures corresponding to a selected grammar represent a semantic template 227. Hence, using the operative grammar 220, speech platform 150 (or another dedicated module, depending on design preferences) maps recognized words to tokens 222 to fill Concept tree(s) of the current semantic template 227. Grammar 220 and the Concept trees can potentially shift after each sentence based on the analysis performed by RCC 135. As indicated at 230, the trees and their concepts 232 accumulate and are filled as sentences are analyzed. Once all of the sentences have been analyzed, the trees have been filled to the extent possible. The user may be prompted to dictate or otherwise enter omitted details.

A representative Concept hierarchy may include the following child nodes:
Abnormality (representing an abnormal finding, such as Cyst, Mass)
AbnormalityDescriptor (such as Morphology, Severity, SignalType)
Measurement (BloodPressure, EjectionFraction, Dimension, etc.)
Anatomy (Brain, Ventricle, Left ventricle, etc.)
AnatomyComponent (Margin, Septa etc.)
Diagnosis (e.g., any pathophysiologic assessment such as Ischemia, Tumor, etc.)
Follow-up recommendation Thus, semantic meaning generation begins when the user speaks into microphone 145. Speech-recognition platform 150 scans digitized speech data in speech buffer 148 and uses the selected grammar 220 to map words to tokens 222. For example, if the user dictates, "There is a simple cyst in the left kidney," speech platform 150, using the selected grammar, generates the tokens "Filler, Cyst, Round, Water- Density, WellCircumscribed, Filler, LeftKidney." Here the phrases "there is a" and "in the" are not relevant, and grammar 220 therefore indicates that they should be treated as "Fillers" and ignored. The phrase "simple cyst" is recognized but it is converted into multiple tokens that identify that it is a Cyst that is round, contains water, and is wellcircumscribed. Finally, the token "LeftKidney" is generated. These particular tokens may be categorized as Names of Items in MCSL 225. Based on the tokens, analysis module 210 selects Concept and lower-level data structures from MCSL 225; that is, it selects data structures containing as many non-filler tokens as possible, and if a selected data structure is not a top-level Concept data structure, it may be integrated within a higher-level data structure or trigger selection of a Concept data structure that includes the token as a node. If MCSL 225 is implemented as a database, then there is a "lookup" of token to Concepts represented in the database. If MCSL 225 is a compiled software class library, then the software technique to create a software object from Class-name is used.

Once the spoken audio has been tokenized and the corresponding Concepts have been created, they are organized into an Observation, on a sentence-by-sentence basis, by SOGS 137. An Observation is the semantic representation of a single unit of medically related concepts as dictated by a physician—e.g., there is a hairline fracture in femur—including all related Concepts. For example, an Observation may be a list of Concepts or a higher-level data structure with Concepts as child nodes. If a new sentence is a continuation of the previous observation, then the concepts of the new sentence are merged with the same Observation. In addition, in some implementations, they may be associated with the patient and stored in patient database 120, which may store all information, including semantic information, specific to each patient.

SOGS 137 includes an analysis module 242 that groups concepts 232 into an Observation data structure. Because the grammar 220 includes a typical set of related Concepts, Observations are tentatively defined by the group of Concepts received by SOGS 137. But an Observation may be refined by an Observation model 244. An Observation model is selected by examining the Observation contents and then automatically choosing or asking the user to choose refinements. For example, if a Cyst is characterized with septa, solids etc., then a Bosniak score can be calculated and added to the Observation as a refinement. If appropriate coronary artery concepts are included in the Observation, a diagnosis of Atherosclerosis can be automatically added. If there is a missing item, e.gl, no Septa identified in the Cyst, then a window to ask the clinician may be displayed with the appropriate choices. Accordingly, an Observation model 244 can be procedure-specific and typically contains the following nodes in an Observation data structure, with Concepts as children of these nodes:

An abnormal finding (or something that is normal), and its associated description Anatomical area (such as Brain etc.) and associated descriptors Diagnosis Devices (such as catheter) and device component (such as tip)

Change from a previous report (such as Increased, stable, etc.)

Follow-up recommendation (e.g., CT in 6 months, or Ablation etc.)

More specifically, based on Observation model 244, analysis module 242 classifies each Concept as the "main" Concept of the Observation or as an associated category. The main concepts are typically Abnormality, Anatomy, Diagnosis, Device, Follow up, etc. Associated categories include Anatomic descriptor, Abnormality Descriptor, Measurement, Shape, Device component (e.g., Tip of a catheter), etc. To support the main and associated categories, SOGS 137 creates a new data structure Observationitem containing two subcomponents that eventually form a tree like structure: KeyConcept, which represents the concept, and Children, which represent associated Concepts. An Observation data structure is then a list of all the Observationitem data structures of the main category. These data structures may be made available to RCC 135 to determine if any changes to grammar 220 are required.

Once a complete Observation has been made (i.e., all tree nodes have been filled or the user has finished dictating), SOGS 137 creates two identifiers: a globally unique identifier (or the identifier associated with a previous observation), and a relative identifier for the particular type of abnormality. For example, if the Observation concerns the first nodule in an anatomic area that may have more than one, then the number 1 is assigned; if it is the second nodule, then number 2, and so on.

Follow-up recommendations may be associated with or certain studies. For example, radiologists routinely dictate follow-up recommendations, so tokens corresponding to common follow-up recommendations may be included (i.e., pre-loaded) in Concept data structures.

Further information may be used by observation model 244 in creating observations 250. As further described below, such information may arrive as text from various sources via an input device 110 or network interface 106. This further information may include a reason 252 for the patient's examination, relevant elements 254 of the patient's medical history, and information 256 concerning the modality of any medical imaging referenced in the user's speech. Such information may be converted into a semantic representation via grammar 220 and enter Concept data structures as node data or may be separately provided to SOGS analysis module 242. Moreover, the additional information 252, 254, 256 may be recognized and used by RCC analysis module 210 in selecting the current grammar 220. Observations 250 are also made available to RCC analysis module 210 for grammar-selection purposes.

The completed Observations are displayed to the user for approval and, upon approval, may be saved in patient database 120. Observations may be formatted into structured narrative reports 260 using conventional routines for converting a data structure into formatted text. If desired, a clinical score 262 (such as Bosniak, TiRads, BiRads, or Syntax) is computed from information in the Observations and is added thereto. Billing codes (e.g., ICD10) may also be identified based on the Observations and added to the report or otherwise provided to the user. For example, billing codes may be associated in MCSL 225 with relevant Concepts and nodes thereof. Storing the associations in a separate database simplifies updates as codes are added, removed or redefined.

Operation of system 100 may be understood with reference to a representative high-level workflow. For convenience, the ensuing discussion focuses on radiology, but it should be understood that the invention has broad applicability across medical specialties as well as applications outside medicine where specialized vocabularies are used.

Consider, first, a traditional workflow. Initially a radiology exam is ordered by a physician treating a patient. The order contains the reason for the exam and any relevant history of the patient. Examples are "headache" for reason and perhaps "high blood pressure," "smoker," or "previous head injury" for relevant history. The order also specifies the type of procedure (MRI of the brain, CT of the abdomen etc.) to be performed. Images are acquired and interpreted by the radiologist, who may review past reports and prior images and compare these with the new images in order to formulate his opinion. The radiologist then generates the report that reflects radiological and pathological observations from the images, as well as any relevant measurements. The radiologist records his impressions including a diagnosis as well as a follow-up recommendation. The report is sent to the ordering physician, who may contact the radiologist for clarification. Then the report is reviewed by a trained coder to add billing codes (e.g., ICD 10 or HCPCS). For some cancer screening reports (lung, mammography, etc.), the report is prepared and sent to national data registries.

An analogous workflow using the system 100 may be organized into steps corresponding to portions of the report that is eventually assembled, beginning with receipt of the reason for exam (e.g., headache, dizziness, cough, chest pain etc.) as text data from an external ordering system, e.g., an order or request directed to the radiology department of a hospital. (That is, in general, it is not dictated by the physician.) The patient history (e.g., smoker, chronic disease, heart disease etc.) is also received as text data from an external ordering system and is converted into its corresponding semantic meaning via speech platform 150 using the current grammar 220. Additionally, because the exam images have already been acquired, system 100 is able to query an imaging archive 118 for information regarding acquired images relevant to the patient and the reason for exam, e.g., data specifying the series description, views, and any other information in order to narrow down the specific imaging sequence vocabulary that could be dictated during the reporting process. This information is also parsed as text input by speech platform 150 using the current grammar 220 to produce tokens 222 that are entered into semantic trees as indicated at 230. In other words, the semantic libraries will contain Concepts associated with images that are collected during the exam and their descriptions in imaging archive 118. Once again, these Concepts are analyzed by RCC 135 to determine whether to alter or change the current grammar 220. For example, in an MRI exam that contains only T1 and T2 sequences, there is no reason to include Diffusion Sequences or Susceptibility Sequences in the current grammar 220. The following is an example of mapping from one commercial MM scanner, which has an associated vocabulary that carries semantic meanings applied to the dictation (along with the semantic meanings associated with the current vocabulary or vocabularies).

| Description from scanner | Semantic meaning (tokens) | Dictation words corresponding to tokens |
| --- | --- | --- |
| T2 EPI HiRes | T2WeightedSequence | T2 Hires, T2 weighted sequence, T2 signal, etc. |
| Sag FSE T2 | SpinEchoSequence, T2WeightedSequence | Spin echo, T2 weighted sequence and synonyms |
| FSE T1 | SPinEchoSequence, T1WeightedSequence | Spin echo, T1 weighted sequence and synonyms |

Additionally, various views of a study (such as AP and Lateral for X-Rays, or Sagittal, Coronal etc. for cross-sectional images) are also acquired. The token mapping described above is also applied to the views that are created to further narrow the semantic context of dictation. Consequently, the tokens corresponding to the dictated words reflect the procedure modality (e.g., Brain MRI, reason for exam, and relevant patient history); the recognition context is created based at least in part on the type of exam (brain vs. chest), reason for exam, and patient history. For example, the procedure "MRI Brain w/o enhancement" retrieves the various components of the head—Brain, Ears, Orbits (eyes) etc. —because even though the procedure indicates Brain, other parts are involved in the scan. These components are represented as additional anatomic Concepts and "enhancement" is a descriptor. Additionally, the current grammar 220 will include tokens corresponding to all the pulse sequences associated with the procedure. The recognition context is based on various types of Concepts that can be included for a given procedure. Signal (e.g., Hyperintense, Hypointense, Isointense, Fluid signal etc.) tokens are also retrieved from SCD 115, although narrowed down to what was acquired. The contents retrieved from SCD 115 may also contain synonyms for the same semantic meaning. The choice of synonyms may be made empirically from automated textual examination of existing reports, the medical literature, etc. The synonyms may be periodically updated (by the system manager or proprietor, or by the user) as new synonyms are discovered.

The speech-recognition grammar retrieved from SCD 115 may be formatted in XML as shown in the following example:

<item>
      <one-of>
      item>
        gradient echo images
      /item>
      item>
        gradient echo sequences
      /item>
      <item>
        G.R.E. images
      /item>
      <item>
        G.R.E. sequences
      /item>
      <item>
        G.R.E. sequence
      </item>
      </one-og>
        <tag>out.ClassName="GradientEchoSequence";
          out.Value="Gradient Echo sequence";<tag>

The above example generates the semantic meaning token "GradientEchoSequence," which is the same as the name in MCSL 225, for various pronunciation synonyms of the gradient echo sequence. The ClassName member of the "out" variable represents a token that maps to a Classification—a lower-level descriptor that defines how tokens are converted to their respective Concepts—in MCSL 225. The token is a character that can be combined with any of multiple semantic components or their relationship, e.g." Severe:Stenosis," as a single token. Once a phrase is recognized, multiple tokens can also be generated for the recognized phrase. Consequently, if the user dictates "Signal Hyperintensity on GRE images in the frontal lobe," the semantic interpretation (Signallndication, Hyperintense, GradientEchoSequence, FrontalLobe) is created by speech platform 150 using the current grammar 220. This sequence of tokens is used to build semantic tree structures that are processed into Observations based on an Observation model 244.

Each Observation (or its constituent Concepts) is analyzed following its creation to determine if the currently loaded grammar needs to change. For example, suppose the user dictates "Right Renal Cyst" in a sentence. Before the user utters the next sentence, RCC 135 causes additional terms such as shape, density, septa, and solid components, which are required for a renal cyst, to be added to grammar 220. These additional terms correspond to tokens in a Renal Cyst semantic object, which will be created as a Concept or an entry therein as dictated by MCSL 225. If, by contrast, the clinician simply dictated the word "cyst" without qualification or elaboration, MCSL 225 would load all possible diseases related to cysts (such as polycystic kidney disease) into the grammar 220. As another example, if the exam is a thyroid ultrasound and the radiologist dictates, "There is a nodule in the upper lobe," RCC 135 adds to grammar 220 the relevant nodule descriptors such as echogenicity, echotexture, shape, margins, etc. as dictated by the associations stored in MCSL 225. It is also possible to manually change the context of dictation using simple spoken control phrases such as, "Set context Kidneys", "Set context Brain," etc. Dictation may be completed by a spoken control phrase, e.g., "Done Dictation." Other command phrases can be added as needed to control the process or to change context.

Temporary and complete Observations for a thyroid exam may be as follows.

| Isthmus Normal Size | Complete Observation |
|---|---|
| 2 mm Nodule | Temporary observation, Start of complete observation, Main ObservationItem (Nodule), Child item 2 mm. |
| Isthmus Normal Size | Complete Observation |
| Upper left lobe | Temporary observation, merged with previous observation |
| 3 mm Nodule | New Abnormality, previous observation is now marked complete, |

A complete "end-to-end" example is as follows. The procedure is a brain MRI without contrast, ordered through a procedure code in an external system. The indication prompting the test is headaches. Based on the procedure, RCC 135 recognizes "brain" as the primary organ but the selected anatomical grammar will include various other anatomical areas (e.g., skull, ears, nose, eyes, mouth, cranial nerves, brain ventricles) because the MRI scan includes them. In addition to the anatomy and sub-anatomy, relevant abnormalities and descriptors are included in the recognition context. The appropriate grammar 220 is loaded into speech platform 150, which then outputs recognized speech text and associated tokens in response to the radiologist's dictation:

"no mass mass effect and midline shift"

"seventh cranial nerve is normal"

"there is a focus of signal abnormality left frontal lobe"

"there are scattered punctate foci of abnormally bright T two signal on cerebral hemispheres"

"this is consistent with age related microvascular ischemic changes"

The recognized speech text and associated tokens, and resulting Observations 250, are as follows:

| | Sentence 1 |
|---|---|
| Dictated speech | no mass mass effect and midline shift |
| Recognized speech | no mass mass effect and midline shift |
| Token Stream | Negative Mass MassEffect Filler MidlineShift |
| Multiple Semantic Observations from single dictation sentence (Token to Semantic Library conversion) | <Abnormality:Mass    AbnormalityDescriptor : Negative    Anatomy:Brain>(defaulted to even though not dictated because the procedure is about the Brain) <Abnormality:MassEffect    AbnormalityDescriptor : Negative    Anatomy:Brain > <Abnormality:MidlineShift    AbnormalityDescriptor : Negative    Anatomy:Brain> |
| | Sentence 2 |
| Dictated Speech | Seventh Cranial Nerve is Normal |
| Recognized Speech | Seventh Cranial Nerve is Normal |
| Token Stream | Ordial 7 CranialNerves Normal |
| Semantic Observation with standardized concept translation. 7th Cranial nerve is FacialNerve | < Abnormality:Normal Anatomy:FacialNerve > |
| | Sentence 3,4 |
| Dictated Speech | There are scattered punctate foci of abnormally bright T two signal on cerebral hemispheres this is consistent with age related microvascular ischemic changes |
| Recognized Speech with text conversion shown in green | There are scattered punctate foci of increased T Two signal on cerebral hemispheres This is consistent with age related microvascular ischemic changes |
| Token Stream Age related is converted to token AgeAppropriate Semantic Observation | Filler Scattered Punctate Focus Measurement:Multiple IncreasedSignal T2WeightedSequence CerebralHemispheres Diagnosis AgeAppropriate MicroVascularIschemicChanges <Abnormality:NonSpecific |

-continued

| | |
|---|---|
| In MRI Radiologists sometimes only dictate signal characteristics instead of a specific abnormality. This means that an abnormality is NonSpecific. | Abnormal Signal: IncreasedSignal Pattern:Focus    Morphology: Scattered    Morphology:Punctate    Measurement:Multiple Series:T2WeightedSequence Anatomy:CerebralHemispheres Link:Diagnosis    Disease:MicroVascularIschemicChanges    Status:AgeAppropriate> |
| Semantic report-list of observations | <Abnormality:Mass    AbnormalityDescriptor : Negative    Anatomy:Brain <Abnormality:MassEffect    AbnormalityDescriptor : Negative    Anatomy:Brain > <Abnormality:MidlineShift    AbnormalityDescriptor : Negative    Anatomy:Brain > < Abnormality:Normal Anatomy:FacialNerve > <Abnormality:NonSpecific   AbnormalSignal: IncreasedSignal   Pattern:Focus     Morphology: Scattered     Morphology :Punctate     Measurement:Multiple   Series:T2WeightedSequence   Anatomy:CerebralHemispheres   Link:Diagnosis     Disease:MicroVascularIschemicChanges     Status:AgeAppropriate> |

The resulting report 260 is as follows:

| Patient: | John Doe, MRN 1001 | | |
|---|---|---|---|
| Indication | Headaches | | |
| Technique | Brain MRI W/O contrast | ICD10-B030YZZ (automatically created) | |
| Findings | Anatomy | Abnormality | Diagnosis |
| | Brain | No mass | |
| | Brain | No mass-effect | |
| | Brain | No mid-line shift | |
| | Facial Nerve | Normal | |
| | Cerebral Hemispheres | Non specific | Age appropriate micro vascular disease |
| | | Increased signal, Foci scattered, punctate T2 Weighted sequences | |
| Impression | Cerebral Hemispheres | Age appropriate microvasculalar disease | ICD10-I67.89 |

Certain embodiments of the present invention are described above. It is, however, expressly noted that the present invention is not limited to those embodiments; rather, additions and modifications to what is expressly described herein are also included within the scope of the invention.

What is claimed is:

1. A medical dictation system comprising:
   a processor;
   circuitry for converting dictated speech into a digitized representation;
   a memory for storing the digitized speech as raw text;
   a semantic context database for storing a plurality of grammars;
   a speech platform for parsing the digitized speech into tokens having semantic content in accordance with a first one one of the stored grammars;
   a recognition context control module, executable by the processor, for analyzing the parsed tokens and replacing the first grammar with a second grammar different from the first grammar and selected from among the stored grammars based on the analysis of the parsed tokens;
   a medical concept semantic library configured for electronic storage of a plurality of semantic templates, each of the semantic templates comprising a plurality of hierarchical data structures each including a root node corresponding to a high-level medical concept specifying at least one of one of (i) an abnormal or normal finding, (ii) an anatomical area, (iii) a diagnosis, (iv) at least one device or device component, (v) a change from a previous report, or (vi) a follow-up recommendation, and at least one subsidiary node, the speech platform being further configured to fill the nodes of the data structures with at least some of the parsed tokens; and
   a facility for transforming the data structures into a structured narrative report in accordance with the second grammar.

2. The system of claim 1, wherein the recognition context controller is configured to retain, alter or replace the first grammar based on raw text corresponding to words of one or more dictated sentences by searching the semantic context database for entries matching the words.

3. The system of claim 2, wherein the processor is configured to analyze the raw text during an interval between spoken sentences.

4. The system of claim 1, wherein the facility comprises a semantic observation generation system, executable by the processor and configured to generate observation data structures by:
   classifying each of the hierarchical data structures as a main concept or an associated concept; and organizing the classified data structures into hierarchical Observationitem data structures, each of the Observationitem data structures including a KeyConcept root node corresponding to the main concept and child nodes corresponding to the associated concepts.

5. The system of claim 4, wherein the recognition context control module is responsive to tokens in the Observationitem data structures in determining whether to alter or replace a current first grammar.

6. The system of claim 4, further comprising a clinical scoring module, executable by the processor, for generating clinical scores based on the observation data structures.

7. The system of claim 4, further comprising a code-generation module, executable by the processor, for generating billing codes based on the observation data structures.

8. The system of claim 5, wherein follow-up recommendations are pre-loaded in main concept data structures.

9. The system of claim 1, further comprising a facility for receiving text corresponding to at least one of a reason for examination, a patient history, or information corresponding to an imaging modality and converting the text into tokens for assignment to the nodes of the data structures.

10. A method of computationally transcribing medical dictation, the method comprising the steps of:
converting dictated speech into a digitized representation;
electronically storing the digitized speech as raw text;
electronically storing, in a semantic context database, a plurality of grammars;
electronically storing a plurality of semantic templates, each of the semantic templates comprising a plurality of hierarchical data structures each including a root node corresponding to a high-level medical concept specifying at least one of one of (i) an abnormal or normal finding, (ii) an anatomical area, (iii) a diagnosis, (iv) at least one device or device component, (v) a change from a previous report, or (vi) a follow-up recommendation, and at least one subsidiary node;
computationally parsing the digitized speech into tokens having semantic content in accordance with a first one one of the stored grammars;
computationally analyzing the parsed tokens and replacing the first grammar with a second grammar different from the first grammar and selected from among the stored grammars based on the analysis of the parsed tokens;
filling the nodes of the data structures with at least some of the parsed tokens; and
transforming the data structures into a structured narrative report in accordance with the second grammar.

11. The method of claim 10, further comprising the step of retaining, altering or replacing the grammar based on raw text corresponding to words of one or more dictated sentences by searching the semantic context database for entries matching the words.

12. The method of claim 11, wherein the step of computationally parsing occurs during an interval between spoken sentences.

13. The method of claim 10, further comprising generating observation data structures according to steps comprising:
classifying each of the hierarchical data structures as a main concept or an associated concept; and
organizing the classified data structures into hierarchical Observationitem data structures, each of the Observationitem data structures including a KeyConcept root node corresponding to the main concept and child nodes corresponding to the associated concepts.

14. The method of claim 13, wherein determining whether to alter or replace a first current grammar is based at least in part on tokens in the Observationitem data structures.

15. The method of claim 13, further comprising the step of computationally generating clinical scores based on the observation data structures.

16. The method of claim 13, further comprising the step of computationally generating billing codes based on the observation data structures.

17. The method of claim 10, further comprising the step of pre-loading follow-up recommendations in main concept data structures.

18. The method of claim 10, further comprising the steps of receiving text corresponding to at least one of a reason for examination, a patient history, or information corresponding to an imaging modality and computationally converting the text into tokens for assignment to the nodes of the data structures.

* * * * *